United States Patent
Bacher et al.

(10) Patent No.: US 9,526,482 B2
(45) Date of Patent: Dec. 27, 2016

(54) MEDICAL INSTRUMENT AND METHOD FOR FITTING TOGETHER A MEDICAL INSTRUMENT

(71) Applicant: Karl Storz GmbH & Co. KG, Tuttlingen (DE)

(72) Inventors: Uwe Bacher, Tuttlingen (DE); Robin Merz, Furtwangen (DE); Sven Schneider, Tuttlingen (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 251 days.

(21) Appl. No.: 13/865,564

(22) Filed: Apr. 18, 2013

(65) Prior Publication Data

US 2013/0310814 A1 Nov. 21, 2013

(30) Foreign Application Priority Data

Apr. 18, 2012 (DE) .................. 10 2012 007 653

(51) Int. Cl.
*A61B 18/14* (2006.01)
*A61B 17/00* (2006.01)
(Continued)

(52) U.S. Cl.
CPC ......... *A61B 17/00234* (2013.01); *A61B 17/00* (2013.01); *A61B 17/29* (2013.01);
(Continued)

(58) Field of Classification Search
CPC ............ A61B 18/1445; A61B 1/00124; A61B 1/00121; A61B 1/00128; A61B 2017/00486; A61B 2018/00172; A61M 39/00
(Continued)

(56) References Cited

U.S. PATENT DOCUMENTS

| | | | |
|---|---|---|---|
| 4,493,646 A | 1/1985 | Lacour et al. | |
| 5,507,297 A * | 4/1996 | Slater | G06M 3/12 600/564 |

(Continued)

FOREIGN PATENT DOCUMENTS

| | | |
|---|---|---|
| DE | 3227417 A1 | 2/1983 |
| DE | 4307539 A1 | 9/1994 |

(Continued)

*Primary Examiner* — Jaymi Della
(74) *Attorney, Agent, or Firm* — Whitmyer IP Group LLC

(57) ABSTRACT

A medical instrument includes an outer shaft, a transmitting device arranged for transferring at least a force or torque and a tool having a coupling device for detachable mechanical connection of the tool and a coupling device on the distal end of the outer shaft and having a transferring coupling device for the detachable mechanical connection of the tool and a tool coupling device on the distal end of the transmitting device. The mechanical connection of the tool coupling device on the outer shaft and the outer shaft coupling device buildable by moving the outer shaft in relation to the tool in a first direction. The mechanical connection of the tool and transfer coupling devices on the transmitting device and device buildable by moving the transmitting device in relation to the tool in a second direction. The first direction opposite to the second direction.

14 Claims, 5 Drawing Sheets

(51) Int. Cl.
 *A61B 17/29* (2006.01)
 *A61B 17/295* (2006.01)
 *A61B 17/32* (2006.01)
(52) U.S. Cl.
 CPC ........ *A61B 17/295* (2013.01); *A61B 17/2909* (2013.01); *A61B 18/1445* (2013.01); *A61B 17/32002* (2013.01); *A61B 2017/00473* (2013.01); *A61B 2017/00477* (2013.01); *A61B 2017/294* (2013.01); *A61B 2017/2931* (2013.01); *A61B 2018/1455* (2013.01); *Y10T 29/49826* (2015.01)
(58) Field of Classification Search
 USPC .......................................................... 606/51
 See application file for complete search history.

(56) References Cited

U.S. PATENT DOCUMENTS

| | | |
|---|---|---|
| 5,817,128 A | 10/1998 | Storz |
| 6,059,719 A | 5/2000 | Yamamoto et al. |
| 6,358,267 B1* | 3/2002 | Murakami et al. ........... 606/205 |
| 2002/0099372 A1* | 7/2002 | Schulze et al. .................. 606/51 |
| 2003/0114839 A1* | 6/2003 | Looper .......... A61B 17/320016 606/1 |
| 2005/0222611 A1* | 10/2005 | Weitkamp ..................... 606/205 |
| 2008/0021278 A1 | 1/2008 | Leonard et al. |
| 2009/0090765 A1 | 4/2009 | Blier et al. |
| 2009/0234378 A1 | 9/2009 | Escudero et al. |
| 2010/0121141 A1 | 5/2010 | Rontal |
| 2011/0276048 A1 | 11/2011 | Kerr et al. |
| 2013/0085516 A1* | 4/2013 | Kerr ................... A61B 18/1442 606/167 |

FOREIGN PATENT DOCUMENTS

| | | | |
|---|---|---|---|
| DE | 9320450 U1 | 9/1994 | |
| DE | 4445105 * | 5/1996 | ............. A61B 17/28 |
| DE | 4445105 A1 | 5/1996 | |
| WO | 9801080 A1 | 1/1998 | |
| WO | 9958066 A1 | 11/1999 | |
| WO | 0054659 A1 | 9/2000 | |
| WO | 2009132359 A2 | 10/2009 | |

* cited by examiner

MEDICAL INSTRUMENT AND METHOD FOR FITTING TOGETHER A MEDICAL INSTRUMENT

FIELD OF THE INVENTION

The present invention is focused on a medical instrument having an outer shaft, a transmitting device and a tool and on a method for fitting together a tool, a transmitting device and an outer shaft to form a medical instrument.

BACKGROUND OF THE INVENTION

The expectations of medical instruments, in particular of medical instruments for micro-invasive procedures, increase continually. Medical instruments having a tool with a gripping or cutting function on the distal end are already provided in a great variety and are widely distributed. Increasingly further functions and degrees of freedom are added, for example rotation of the tool about the longitudinal axis of the shaft, an ability to bend the shaft proximally of the tool or a second, independently controllable acting device on the tool. A second transferring element can be provided in the shaft of the medical instrument to control said further functions or degrees of freedom, for example a second transferring rod.

In the case of medical instruments that can be used multiple times, an ability to be taken apart as extensively as possible as a prerequisite for total cleaning is particularly important. In this case, it can be noticed that a growing number of functions and degrees of freedom requires an ever more extensive ability to be taken apart or an ability to be taken apart into ever more individual parts. At the same time, it should be possible to handle all the individual parts and to take apart and to fit together the medical instrument as reliably as possible and in a simple and intuitive manner or with a small amount of expenditure on training. In particular, it should be possible to take it apart with as few steps as possible. In this case, it is helpful when the medical instrument has as few actuating devices as possible for unlocking the mechanical connections of the individual parts.

SUMMARY OF THE INVENTION

An object of the present invention is to create an improved medical instrument having an outer shaft, a transmitting device and a tool and to create an improved method for fitting together a tool, a transmitting device and an outer shaft to form a medical instrument.

A medical instrument includes an outer shaft, a transmitting device to be arranged in the outer shaft for transferring at least either a force or a torque and a tool having an outer shaft coupling device for the detachable mechanical connection of the tool and a tool coupling device on the distal end of the outer shaft and having a transferring coupling device for the detachable mechanical connection of the tool and a tool coupling device on the distal end of the transmitting device, wherein the mechanical connection of the tool coupling device on the outer shaft and the outer shaft coupling device on the tool is buildable by means of a movement of the outer shaft in relation to the tool in a first direction, wherein the mechanical connection of the tool coupling device on the transmitting device and the transferring coupling device on the tool is buildable by means of a movement of the transmitting device in relation to the tool in a second direction, and wherein the first direction is opposite to or is non-parallel to the second direction.

The medical instrument is, in particular, a micro-invasive surgical instrument. The medical instrument can have further component parts in addition to the outer shaft, the transmitting device and the tool or can be provided for combination with or to fit together with further component parts. In particular, the medical instrument can include a handling device or can be provided and realized to fit together with a handling device.

The outer shaft can be straight or curved, rigid or flexible. The transmitting device is, for example, a transferring rod or an inside shaft, it being possible for a further transmitting device in the form of a transferring rod to be arranged in a substantially tubular inside shaft. The transmitting device, in turn, can be straight or curved, rigid or flexible. If the outer shaft is curved or flexible, the transmitting device is, in particular, at least flexible in part in order to be able to be moved, in particular displaced and/or rotated, in the curved outer shaft.

The tool has, in particular, several functions which are able to be controlled independently of one another by means of several transmitting devices. For example, a first function of the tool is controlled by means of a transferring rod and a second function of the tool is controlled by means of an inside shaft.

The first direction and the second direction are, in particular, opposing translatory or opposing rotatory directions. Through the detachable mechanical coupling between the tool, on the one hand, and the outer shaft and, on the other hand, the transmitting device with movements in opposing directions, both mechanical connections can be locked by the outer shaft and the transmitting device being locked together with respect to a relative movement parallel to the first and second direction.

As an alternative to this, the first direction is non-parallel to the second direction, in particular at right angles to the second direction. A rotational movement is at right angles to a translational movement along the rotational axis of the rotational movement insofar as in the case of a rotational movement—when seen from the points on the rotational axis—all points are moved at all times in directions at right angles to the rotational axis. For example, the mechanical connection of the tool coupling device on the outer shaft and the outer shaft coupling device on the tool are buildable by means of a translatory movement of the outer shaft in relation to the tool and the mechanical connection of the tool coupling device on the transmitting device and the transferring coupling device on the tool are buildable by means of a rotational movement of the transmitting device in relation to the tool. Or in reverse, the mechanical connection of the tool coupling device on the outer shaft and the outer shaft coupling device on the tool are buildable by means of a rotational movement of the outer shaft in relation to the tool and the mechanical connection of the tool coupling device on the transmitting device and the transferring coupling device on the tool are buildable by means of a translational movement of the transmitting device in relation to the tool. The rotational axis of the rotational movement, in this case, is in particular parallel to the direction of movement of the translatory movement.

In the case of a medical instrument having the described features, consequently two mechanical connections, namely that between the tool and the outer shaft on the one hand and the transmitting device on the other hand, can be locked by means of one single device. Said locking can be effected, moreover, on the proximal ends of the outer shaft and the transmitting device such that installation space can be saved on the distal ends thereof.

In the case of a medical instrument, as is described here, in particular, the mechanical connection of the tool coupling device on the outer shaft and the outer shaft coupling device on the tool is buildable by means of a rotation of the outer shaft in relation to the tool in a first direction and the mechanical connection of the tool coupling device on the transmitting device and the transferring coupling device on the tool is buildable by means of a rotation of the transmitting device in relation to the tool in a second direction.

In the case of a medical instrument, as is described here, in particular at least either the outer shaft coupling device on the tool and the tool coupling device on the outer shaft or the transferring coupling device on the tool and the tool coupling device on the transmitting device include screw threads.

In particular, the outer shaft coupling device on the tool and the tool coupling device on the outer shaft in each case include left-handed thread and the transferring coupling device on the tool and the tool coupling device on the transmitting device include in each case right-handed thread or vice versa.

In the case of a medical instrument, as is described here, in particular at least either the outer shaft coupling device on the tool and the tool coupling device on the outer shaft or the transferring coupling device on the tool and the tool coupling device on the transmitting device include bayonet couplings.

In particular, bayonet couplings are already used on conventional medical instruments which can be taken apart and are consequently subject to a high level of structural and manufacturing control. Compared to the conventional locking of each individual bayonet coupling by means of a locking bar on the bayonet coupling itself (often also referred to as a pendulum plate) or by means of a locking bar on the proximal end of the medical instrument (often also referred to as a "half-shell" solution), a medical instrument having the features described here makes one single locking device possible for two bayonet couplings and consequently provides a clear saving on installation space and on expenditure spent on construction and manufacturing.

In the case of a medical instrument, as is described here, the transmitting device includes, in particular, an inside shaft.

A medical instrument, as is described here, additionally includes, in particular, a transferring rod for transferring at least either a force or a torque, wherein the transferring rod is realized for controlling a first function and the inside shaft is realized for controlling a second function.

It is applicable to both the inside shaft and the transferring rod that, in the case of a curved or curvable or flexibly elastic outer shaft, they are realized in particular at least in portions so as to be flexibly elastic. The transferring rod is arranged, in particular, in the interior or in the lumen of the tubular inside shaft. The inside shaft is arranged, in particular, in the ring-shaped space between the outer shaft and the transferring rod.

The first function to be controlled by means of the transferring rod is, for example, a gripping function.

The second function to be controlled by means of the inside shaft rod is, in particular, a cutting function.

In the case of a medical instrument, as is described here, in particular the transferring rod is coupled with a pivotable mouth part of the tool and the inside shaft is realized for a mechanical connection to a cutting device of the tool.

In particular, the distal end of the transferring rod is coupled in such a manner with one or several pivotable mouth parts that a movement (in particular a translatory movement parallel to the longitudinal axis of the outer shaft) of the transferring rod brings about a pivoting of the pivotable mouth part or parts each about a pivot axis at right angles to the longitudinal axis of the outer shaft. The cutting device is, in particular, a blade or scalpel which is displaceable in the tool in the direction parallel to the longitudinal axis of the outer shaft. The mouth parts are realized, in particular, such that even in the closed or gripping configuration of the mouth parts, between them there remains a channel or a lumen in which the cutting device is movable in order to cut through tissue gripped by means of the mouth parts. In this case, the cutting device is mounted, in particular, such that it is not rotatable about the longitudinal axis of the tool or of the outer shaft. In particular, the cutting device is arranged in a groove in the transferring rod and in the tool, the groove having a substantially rectangular cross section which corresponds to the cutting device.

As an alternative to this, the medical instrument can have two transferring rods for controlling two arbitrary functions of the tool which differ from one another, at least one transferring rod and the outer shaft being coupleable with the tool by means of the above-described movements which are in opposite directions to one another.

In the case of a medical instrument, as is described here, the transferring coupling device on the tool includes, in particular, a projection which protrudes in a direction at right angles with respect to the provided direction of movement of the cutting device, the tool coupling device on the transmitting device including an L-shaped slot or an L-shaped groove for accommodating the projection.

The projection and the L-shaped slot or the L-shaped groove form bayonet coupling devices which correspond to one another, the projection on the cutting device having the function of a carrier or claw. The projection is arranged, in particular, on the proximal end or close to the proximal end of the cutting device. If the cutting device, as described above, is arranged in a groove in a transferring rod, the projection is realized, in particular, such that it projects beyond the edges of the groove, other regions of the cutting device being arranged completely in the groove. The bayonet-like coupling between the cutting device and the transmitting device can be realized with a particularly small requirement for space.

In the case of a medical instrument, as is described here, the tool has, in particular, two mouth parts which are electrically insulated from one another, a first of the two mouth parts which are electrically insulated from one another being connected so as to be electrically conductive, and a second of the two mouth parts which are electrically insulated from one another being connected to the outer shaft so as to be electrically conductive.

Consequently, the medical instrument can be used, in particular, in electro-surgery. In electro-surgery or electro-surgical procedures, (Joule) heat is generated in the tissue by means of current flow and as a result of the electric resistance of the tissue. The current flow is localized as precisely as possible by the form and arrangement of the electrodes used in this case, in particular of two or more mouth parts. Through the heat generated, the tissue traversed by the current is sclerosed or destroyed. As a result, tissues can be glued or closed and bleeding stopped.

As a rule, high frequency alternating currents are used in electro-surgery in order to avoid stimulation of nerves and other unwanted secondary actions. The terms "electro-surgery" and "HF surgery" are consequently often used synonymously. A further term often used synonymously is that of electro-cauterization.

A medical instrument having the features described here can make it possible to grip vessels or other tissue, to electro-cauterize the gripped tissue and to cut it subsequently by means of the cutting device. On account of the described mechanical connection of the tool and the outer shaft and the transmitting device, said functions can be realized, in spite of an ability to be taken apart, with a comparatively small cross section of the shaft and of the tool.

In the case of a medical instrument, as is described here, the inside shaft has, in particular, a distal portion and a proximal portion which is electrically insulated from the distal portion.

In particular, the inside shaft is not a component part of the electric circuit. Where a distal portion is electrically insulated from a proximal portion of the inside shaft, the distal portion of the inside shaft can be connected to the transferring rod so as to be electrically conductive and at the same time the proximal portion of the inside shaft can be connected to the outer shaft so as to be electrically conductive without creating, as a result, an electrically conductive connection of the transferring rod and the outer shaft. As a result, both the distal portion of the inside shaft with a bayonet coupling device or another tool coupling device for the mechanical connection to the tool (in particular the above-described cutting device) and the proximal portion of the inside shaft can be formed from metal and consequently have great strength, great hardness and favorable wear characteristics. This can be advantageous on the proximal end of the inside shaft, in particular with respect to the recess described below which corresponds to a locking bar on the outer shaft.

A medical instrument, as is described here, includes additionally, in particular, a handling device for the detachable mechanical connection to the proximal ends of the outer shaft and of the transmitting device, wherein the handling device, the outer shaft and the transmitting device are realized such that the outer shaft and the transmitting device are not movable in relation to one another in a parallel manner with respect to the first and to the second direction when they are mechanically connected to the handling device in a provided manner.

The prevention of the movement of the outer shaft and the transmitting device in relation to one another in a parallel manner with respect to the first and to the second direction is also referred to below as the locking together of the outer shaft and the transmitting device. Said locking does not exclude the outer shaft and the transmitting device being movable in relation to one another in a direction at right angles to the first and to the second direction. Similarly, the locking of the outer shaft and the transmitting device together does not exclude these being movable together in a direction parallel and/or at right angles to the first and to the second direction.

On account of the opposite movements necessary for connecting and consequently also for separating the mechanical connection of the tool and the outer shaft, on the one hand, and the transmitting device, on the other hand, the locking of the outer shaft and the transmitting device together brings about a locking of the mechanical connections between the tool, on the one hand, and the outer shaft and the transmitting device, on the other hand. Consequently, just a mechanical connection of the proximal ends of the outer shaft and of the transmitting device to the handling device in the provided manner, in particular locking of the outer shaft on the handling device, can at the same time bring about locking of the mechanical connections between the tool, on the one hand, and the outer shaft and the transmitting device, on the other hand.

In the case of a medical instrument, as is described here, the outer shaft includes, in particular, a locking bar which is movable between an unlocking position and a locking position and is realized in order to engage in a corresponding recess on the transmitting device in the locking position, the handling device being realized in order to hold the locking bar in the locking position when the outer shaft is mechanically connected to the handling device.

The locking bar on the outer shaft is also referred to as a half shell. The locking bar is movable, in particular in the radial direction between the radially outside unlocking position and the radially inside locking position. The locking bar is realized, in particular, in order to protrude beyond the outer contour of the outer shaft in the unlocking position and to close off in a substantially flush manner with the outside contour of the outer shaft in the locking position.

One or more O-ring seals, leaf springs or other elastic elements can be provided and realized in order to exert a force onto the locking bar in the direction of the locking position. When the outer shaft is connected to the handling device in the provided and predetermined manner, it is accommodated, for example, in a recess with a corresponding cross section. In this case, the inside surface of the recess, in particular, abuts against a radially outside surface of the locking bar and, in this manner, holds it in the locking position.

When the first direction and the second direction are in each case parallel or substantially parallel to the circumferential direction (in particular in the case of screw thread couplings or bayonet couplings), the recess extends in the axial direction in particular in the form of a groove or a flattening on the transmitting device and consequently at right angles to the first and to the second direction. The recess extends, in particular, so far in the axial direction that the outer shaft and the transmitting device are movable in relation to one another in the axial direction inside a predetermined region.

When the first direction and the second direction are in each case parallel to the axial direction, the recess is realized, in particular, as a groove which extends in the circumferential direction on the transmitting device. As a result, the outer shaft and the transmitting device can be rotated in relation to one another.

In the case of a medical instrument, as is described here, the outer shaft and the inside shaft are movable in particular together in the direction parallel to the first and to the second direction in relation to the handling device when they are mechanically connected to the handling device.

In particular in the case of bayonet couplings between the tool, on the one hand, and the outer shaft and the transmitting device, on the other hand, this makes it possible for the tool to rotate about its longitudinal axis or about the longitudinal axis of the outer shaft.

In the case of a method for fitting together a tool, a transmitting device for transferring at least either a force or a torque and an outer shaft to form a medical instrument, the transmitting device is mechanically connected to the tool, wherein the connecting process includes moving the transmitting device in a first direction in relation to the tool, and the outer shaft is mechanically connected to the tool, wherein the connecting process includes moving the outer shaft in a second direction in relation to the tool, and wherein the first direction is opposite to or is non-parallel to the second direction.

The tool, the transmitting device, the outer shaft and the medical instrument formed therefrom have, in particular, the above-described features. The method for fitting together can serve for the preparation of the medical instrument, in particular also for the preparation of the application of the medical instrument within the framework of a diagnostic, surgical or therapeutic method. The method for fitting together does not itself, however, represent any diagnostic, surgical or therapeutic method.

In the case of a method, as is described here, additionally, in particular, the proximal end of the outer shaft and the proximal end of the transmitting device are coupled in such a manner that the outer shaft and the transmitting device are not movable in relation to one another in a parallel manner with respect to the first and to the second direction.

The proximal end of the outer shaft and the proximal end of the transmitting device are coupled with the tool in particular once the inside shaft and the outer shaft have been mechanically connected. The coupling of the proximal ends of the outer shaft and of the transmitting device does not exclude, in particular, the outer shaft and the transmitting device from being movable together parallel to the first and to the second direction. In addition, the coupling of the proximal ends of the outer shaft and of the transmitting device does not exclude, in particular, the outer shaft and the transmitting device from being movable in relation to one another at right angles to the first and to the second direction.

In the case of a method, as is described here, additionally, in particular, the proximal end of the outer shaft is mechanically connected to a handling device, wherein the proximal ends of the outer shaft and of the transmitting device are coupled together during the process of connecting the proximal end of the outer shaft to the handling device.

The proximal end of the outer shaft is connected to the handling device in particular once the inside shaft and the outer shaft have been mechanically connected to the tool.

BRIEF DESCRIPTION OF THE DRAWINGS

Embodiments are explained below by way of the accompanying Figures, in which, in detail.

DETAILED DESCRIPTION OF THE INVENTION

Figure 1:
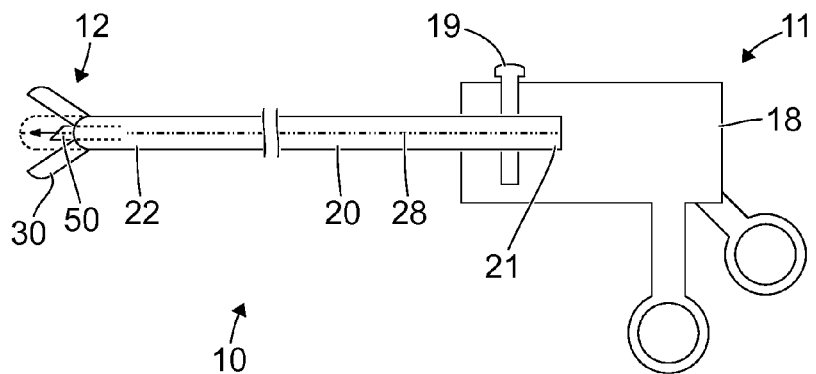
FIG. 1 shows a schematic representation of a medical instrument.

FIG. 1 shows a schematic representation of a medical instrument 10 having a proximal end 11 and a distal end 12. On the proximal end 11, the medical instrument 10 has a handling device 18 which is realized for the purpose of being held with one hand by medical personnel and absorbing manually generated forces and torques. To this end, the handling device 18 has, in particular, several gripping parts which are movable at least in part in relation to one another.

A shaft 20 extends from the proximal end 11 or from the handling device 18 as far as up to the distal end 12 of the medical instrument 10. The shaft 20 has a proximal end 21 and a distal end 22. The proximal end 21 of the shaft 20 is mechanically connected to the handling device 18, in particular is arranged in a recess by way of a development which corresponds to the proximal end 21 of the shaft 20 and is locked there in a positive locking manner by means of a locking device 19.

The shaft 20 has a longitudinal axis 28. Where the shaft 20 is developed in a circular cylindrical manner, the longitudinal axis 28 is, in particular, the axis of symmetry of the lateral surface of the shaft 20. The below-described inside construction of the shaft 20 can also be rotationally symmetrical with respect to the longitudinal axis 28. The shaft 20 can be straight or—deviating from the representation in FIG. 1—curved, rigid or flexible. When the shaft 20 is curved or flexible at least in portions, the term longitudinal axis refers below to the longitudinal axis of the shaft 20 on its proximal end 21 or on its distal end 22. The shaft 20 is rotatable about its longitudinal axis 28 in particular even in the state locked in the handling device 18.

The distal end 22 of the shaft 20 is connected to a tool which includes a gripping device 30 and a cutting device 50. The gripping device 30 has, in particular, two gripping jaws, at least one of which is pivotable about a pivot axis at right angles with respect to the drawing plane of FIG. 1. In the case of the example shown in FIG. 1, the two gripping jaws are pivotable between open positions, which are shown in FIG. 1 by continuous lines, and closed positions, which are shown in FIG. 1 by broken lines. As indicated by an arrow in FIG. 1, the cutting device 50 is movable in the direction parallel to the longitudinal axis 28 both when the mouth parts of the gripping device assume their open positions and also when they assume their closed positions.

Exemplary embodiments of the tool 30, 50 and of its detachable mechanical connection to an outer shaft, an inside shaft and a transferring rod are shown below. The tools, outer shafts, inside shafts and transferring rods shown below can be realized and used to form a medical instrument having the features shown by way of FIG. 1 and/or having other features.

Figure 2:
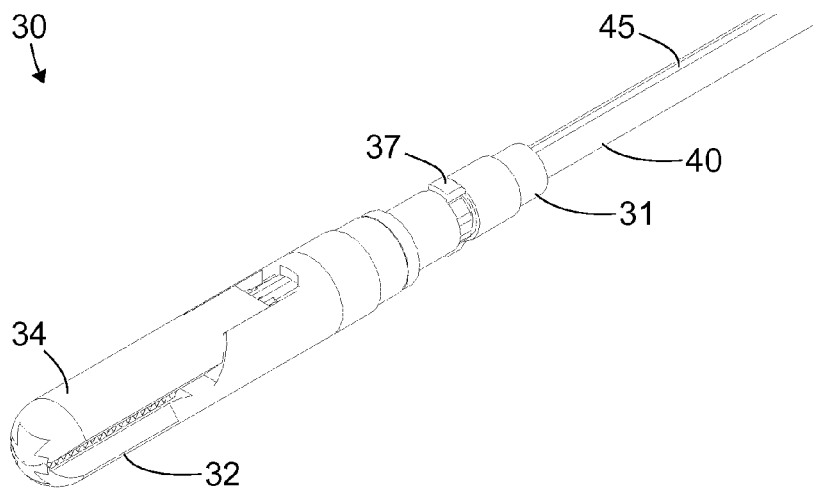
FIG. 2 shows a schematic axonometric representation of a gripping device for a medical instrument.

FIG. 2 shows a schematic axonometric representation of a gripping device 30 which is provided and realized for forming a medical instrument, as is shown above by way of FIG. 1. The gripping device 30 has a proximal end 31 and two mouth parts 32, 34 which forms the distal end of the gripping device 30. Contrary to the gripping device indicated in FIG. 1, the gripping device 30 shown in FIG. 2 includes a fixed mouth part 32 and a pivotable mouth part 34. Close to the proximal end 31, the gripping device 30 has two symmetrically arranged bayonet jaws or carriers 37, one of which is arranged on a side facing away from the observer and is consequently extensively hidden.

The gripping device 30 is mechanically connected to a transferring rod 40. The transferring rod 40 is movable in the axial direction, i.e. parallel to the longitudinal axis of the transferring rod 40 and to the longitudinal axis 28 of the shaft 20 (cf. FIG. 1), within a predetermined interval in relation to the gripping device 30, in particular in relation to the proximal end 31 and to the fixed mouth part 32. The distal end of the transferring rod 40, which is arranged inside the gripping device 30 and is consequently not visible in FIG. 2, is coupled with the pivotable mouth part 34 in such a manner that an axial movement of the transferring rod 40 is combined with a pivoting movement of the pivotable mouth part 34. A groove 45, which, in particular, has a narrow and deep rectangular cross section, is provided in the transferring rod 40. The groove 45 in the transferring rod 40, on the distal end thereof which cannot be seen in FIG. 2, is continued by a channel with a corresponding cross section which extends between the mouth parts 32, 34 as far as almost up to their distal ends.

Parts of the gripping device 30, in particular the carriers 37 and the transferring rod 40, are produced from high-grade steel or another metal. The carriers 37 and the transferring rod 40 are insulated electrically from one another. The mouth parts 32, 34 have metal and consequently electrically conductive gripping faces which are insulated electrically from one another when they do not abut against one another, as shown in FIG. 2. The carriers 37 and the transferring rod 40 are in each case connected to the gripping face of a mouth part 32, 34 so as to be electrically conductive. In particular, the carriers 37 are connected to the gripping face of the fixed mouth part 32 so as to be electrically conductive and the transferring rod 40 is connected to the gripping face of the pivotable mouth part 34 so as to be electrically conductive.

Figure 3:
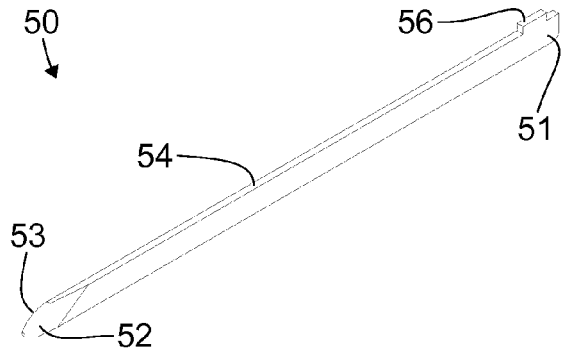
FIG. 3 shows a schematic axonometric representation of a cutting device.

FIG. 3 shows a schematic axonometric representation of a cutting device 50 having a proximal end 51 and a distal end 52. On the distal end 52, the cutting device 50 has a cutting edge 53. On the proximal end, the cutting device 50 has a projection 56. Between the proximal end 51 and the distal end 52, the cutting device includes a rod-shaped region 54 which is essentially in the form of a strip-shaped plate or a bar with a rectangular cross section.

Between the projection 56 on the proximal end 51 and the cutting edge 53 on the distal end 52, the cross section of the cutting device 50 corresponds substantially to the cross section of the groove 45 in the transferring rod 40 (cf. FIG. 2) such that the cutting device 50, apart from the projection 56, is accommodated completely by the groove 45 in the transferring rod 40 and is guided in said groove low in play and friction and can be displaceable in the longitudinal direction of the transferring rod 40 and of the cutting device 50. The projection 56 is provided in order to project from the groove 45 in the transferring rod 40.

Figure 4:
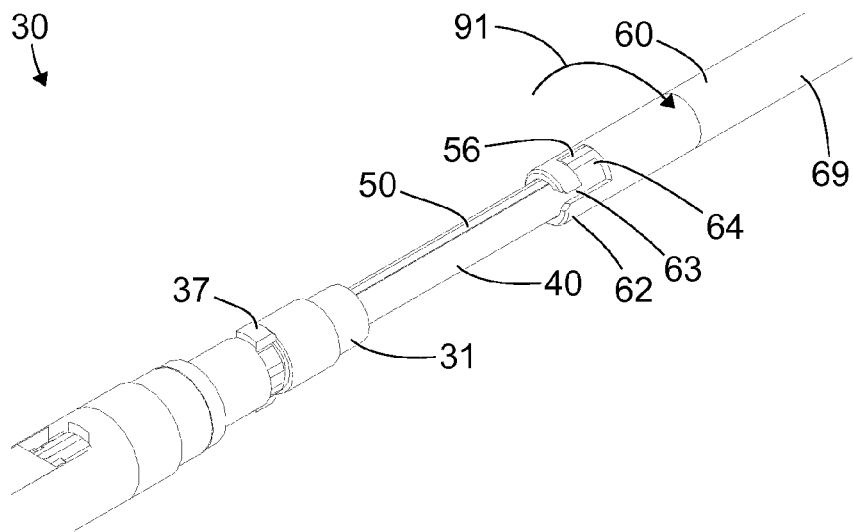
FIG. 4 shows a further schematic axonometric representation of the devices from FIGS. 2 and 3.

FIG. 4 shows a further schematic axonometric representation of the gripping device from FIG. 2 and of the cutting device 50 from FIG. 3. In the case of the representation in FIG. 4, the cutting device 50 is arranged in the groove 45 in the transferring rod 40 (cf. FIG. 2). The distal end 52 of the cutting device 50 (cf. FIG. 3), in this case, is arranged in the gripping device and, in particular, between the mouth parts 32, 34. The projection 56 projects out of the groove 45.

FIG. 4 additionally shows an inside shaft 60 which essentially has a tubular development or is shaped in the form of a regular cylinder. On its distal end 62, the inside shaft 60 has an L-shaped slot with an axial portion 63 or a portion 63 extending in the axial direction and a circumferential portion 64 or a portion 64 extending in the circumferential direction. The width of the axial portion 63, to be measured in the circumferential direction, and the width of the circumferential portion 64 of the L-shaped slot, to be measured in the axial direction, are adapted to the dimensions of the projection 56 on the cutting device 50.

Once the transferring rod 40 has been inserted into the inside shaft 60, the projection 56 can be inserted through the axial portion 63 as far as into the circumferential portion 64 by means of a relative movement in the axial direction. When the projection 56 on the cutting device 50 is located in the circumferential portion 64 of the L-shaped slot on the distal end 62 of the inside shaft 60, the inside shaft 60 can be rotated in relation to the gripping device 30, the transferring rod 40 and the cutting device 50 in a first direction 91 as far as up to the configuration shown in FIG. 4.

In the relative positioning of the cutting device 50 and of the inside shaft 60 shown in FIG. 4, the cutting device 50 and the inside shaft 60 are coupled together in a rigid manner (apart from play) with respect to axial movements. An axial movement of the inside shaft 60 is consequently combined with a corresponding axial movement of the cutting device 50. Consequently, a movement of the cutting edge 53 on the distal end 52 of the cutting device 50 (cf. FIG. 3) in the mentioned channel between the mouth parts 32, 34, which is not visible in the Figures, can be brought about by means of the inside shaft 60 in order to cut tissue which is gripped, for example, by the mouth parts 32, 34 after electro-cauterization.

The inside shaft 60 has an insulating casing 69, the distal edge of which lies close to the L-shaped slot 63, 64 and which can extend almost up to the proximal end of the inside shaft 60.

Figure 5:
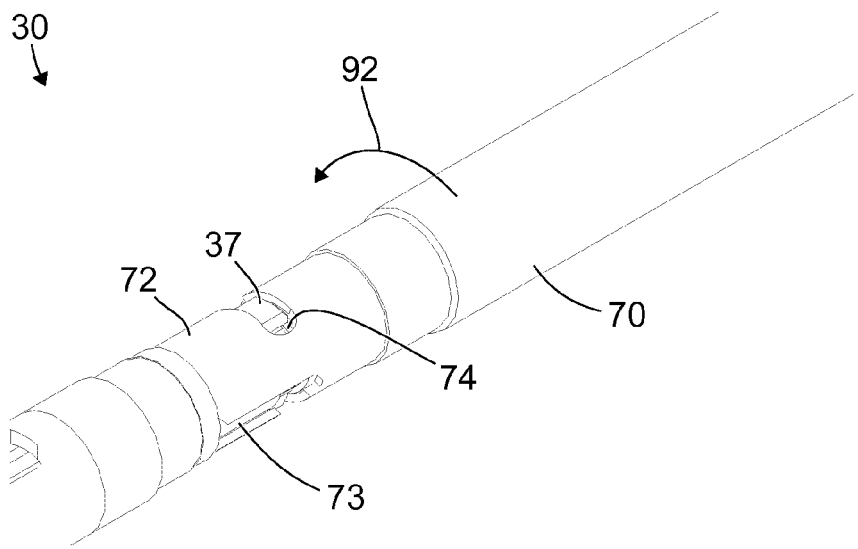
FIG. 5 shows a further schematic axonometric representation of the devices from FIGS. 2 to 4.

FIG. 5 shows a further schematic axonometric representation of the gripping device 30 from FIGS. 2 and 4. The representation in FIG. 5 differs from the representation in FIGS. 2 and 4 in that an outer shaft 70 is coupled with the gripping device 30. At its distal end 72, the outer shaft 70 has two symmetrically arranged L-shaped slots each with an axial portion 73 and a circumferential portion 74. In FIG. 5, both L-shaped slots are partially visible, and specifically the axial portion 73 of one L-shaped slot is visible while the circumferential portion 74 of the other L-shaped slot is visible.

The width of the axial portions 73 to be measured in the circumferential direction and the width of the circumferential portions 74 of the L-shaped slots to be measured in the axial direction are adapted to the dimensions of the carriers 37 on the gripping device 30. Through a movement of the outer shaft 70 in the axial direction and subsequent rotation in relation to the gripping device 30, the carriers 37 can be inserted through the axial portions 73 into the circumferential portions 74 as far as up to the configuration shown in FIG. 5. In the case of the configuration or arrangement of the carriers 37 in the circumferential portions 74 of the L-shaped slots on the distal end 72 of the outer shaft 70 shown in FIG. 5, the outer shaft 70 and the gripping device 30 are coupled together in a rigid manner (apart from play) with respect to axial forces and movements.

Comparing FIGS. 4 and 5, it can be seen that the circumferential portions 64, 74 of the L-shaped slots on the distal ends 62, 72 of the inside shaft 60, on the one hand, and of the outer shaft 70, on the other hand, extend from the axial portions 63, 73 in opposite directions. In a corresponding manner, the direction 92, in which the outer shaft 70 is to be rotated in relation to the gripping device 30 in order to achieve the coupled configuration shown in FIG. 5, is opposite to the direction 91 in which the inside shaft 60 is to be rotated in relation to the gripping device 30 and to the cutting device 50 in order to achieve the coupled configuration shown in FIG. 4.

Figure 6:
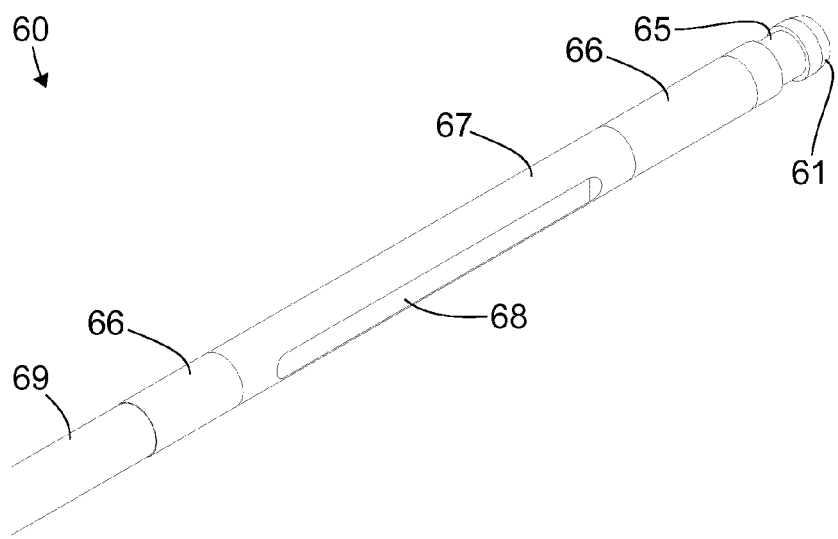
FIG. 6 shows a schematic axonometric representation of a proximal end of an inside shaft.

FIG. 6 shows a schematic axonometric representation of a proximal region of the inside shaft 60 from FIG. 4. On its proximal end 61, the inside shaft 60 has a metal coupling component 65 for the detachable, direct or indirect mechanical coupling with a movable gripping part of a handling device. The coupling component 65 is mechanically connected in a rigid manner to a metal component 67 by means of an insulating component 66 and at the same time is insulated electrically from said component. The metal component 67 has two flattenings 68, which are arranged symmetrically with respect to one another, only one of which is facing the observer in FIG. 6 and is consequently visible. By means of a further insulating component 66, the metal component 67 is mechanically connected to a metal tube, which is surrounded by the insulating covering 69 and extends as far as up to the distal end 62 shown in FIG. 4, and is insulated electrically from said tube.

Figure 7:
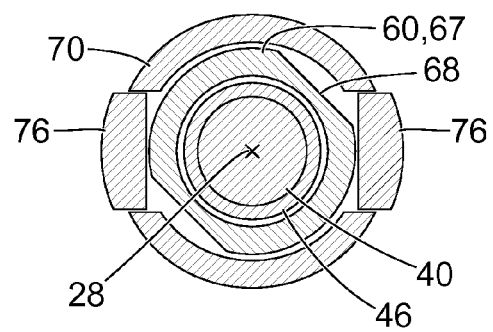
FIG. 7 shows a schematic sectional representation of a shaft.

FIG. 7 shows a schematic representation of a section through the transferring rod 40, the inside shaft 60 and the outer shaft 70 in the region of the metal component 67 of the inside shaft 60 (cf. FIG. 6). The sectional plane shown is at right angles to the longitudinal axis 28 (cf. FIG. 1). In the sectional plane shown, the transferring rod 40 has an insulating covering 46 which insulates the transferring rod 40 electrically from the inside shaft 60. The outer shaft 70 has two openings which are situated opposite one another, in which locking bars 76 are arranged so as to be radially displaceable. The locking bars 76 are pressed radially inward for example by one or several O-ring seals, leaf springs or other elastic devices and/or are held in the recesses in the outer shaft 70 by other devices not shown in FIG. 7.

Figure 8:
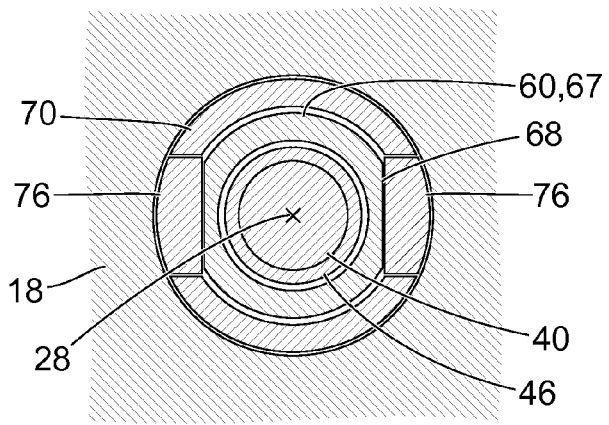
FIG. 8 shows a further schematic sectional representation of the shaft from FIG. 7.

FIG. 8 shows a further schematic sectional representation of the transmitting device 40, of the inside shaft 60 and of the outer shaft 70. The sectional plane shown in FIG. 8 corresponds to the sectional plane of FIG. 7. The representation in FIG. 8 differs from the representation in FIG. 7, in particular, in that the inside shaft 60 is rotated about the longitudinal axis 28 so far that the locking bars 76 can be displaced radially inward and abut against the flattenings 68 on the metal component 67 of the inside shaft 60. In this case, the locking bars 76 close off flush with the circular outer contour of the outer shaft 70. In said configuration, the outer shaft 70 with the locking bars 76, the inside shaft 60 and the transferring rod 40 can be inserted into a corresponding recess in the handling device 18 (cf. FIG. 1) in order to achieve the configuration shown in FIG. 8.

In the case of the configuration shown in FIG. 8, radially outside faces of the locking bars 76 abut against the inside surface of the recess in the handling device 18 and radially inside surfaces of the locking bars 76 abut against the flattenings 68 on the metal component 67 of the inside shaft 60. As a result, radial movements of the locking bars 76 and a rotation of the inside shaft 60 about the longitudinal axis 28 in relation to the outer shaft 70 are prevented in a positive locking manner. As a result, the mechanical connection, shown above by way of FIG. 4, between the distal end 62 of the inside shaft 60 and the cutting device 50 and the mechanical connection, shown above by way of FIG. 5, between the outer shaft 70 and the gripping device 30 are locked at the same time. The outer shaft 70 and the inside shaft 60 can, however, be rotated together about the longitudinal axis 28.

Consequently, the locking bars 76 in the representation in FIG. 7 assume unlocking positions and in the representation in FIG. 8 they assume locking positions.

The length of the locking bars 76, measured in the axial direction or parallel to the longitudinal axis 28, is shorter, in particular clearly shorter than the length of the flattening 68 on the metal component 67 shown in FIG. 6. As a result, a relative movement of the inside shaft 60 and the outer shaft 70 is possible in the axial direction.

Deviating from the representations in FIGS. 6 to 8, the metal component 67 can have just one flattening 68 and just one locking bar 76 can be provided in the outer shaft 70.

Figure 9:
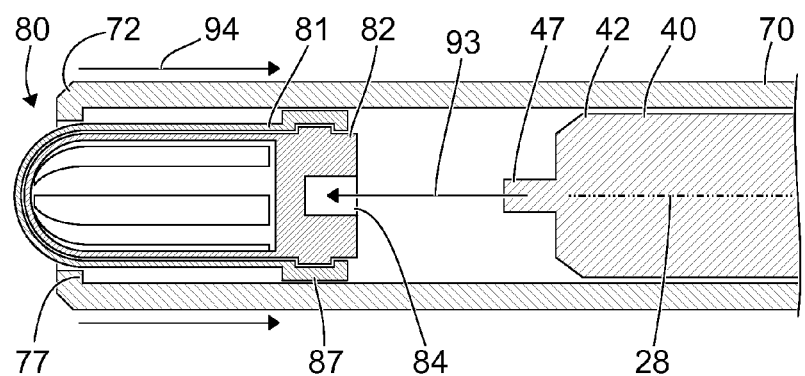
FIG. 9 shows a schematic sectional representation of a further tool for a medical instrument.

FIG. 9 shows a schematic sectional representation of a further tool 80. The sectional plane of FIG. 9 includes the longitudinal axis 28 (cf. FIG. 1). Unlike as indicated in FIG. 1 and contrary to the example in FIGS. 2 to 8, the tool 80 does not have any pivotable mouth parts or an axially movable cutting device. Instead of which, the tool 80 includes an outside, cage-shaped first component part 81 and an inside, also cage-shaped second component part 82. The second component part 82 is rotatable in relation to the first component part 81 about the longitudinal axis 28 in order to sever off tissue which projects through openings in the component parts 81, 82.

Close to its proximal end on the first component part 81, the tool 80 has an outwardly projecting collar 87 and on the second component part 82 it has a recess 84. The collar 87 and the recess 84 are in each case not rotationally symmetrical with respect to the longitudinal axis 28.

On its distal end 72, an outer shaft 70 has an inwardly projecting collar 77 with a development which corresponds to the collar 87 on the first component part 81 of the tool 80. On its distal end 42, a transferring rod 40 has a coupling 47 with a development which corresponds to the recess 84 on the second component part 82 of the tool 80.

Figure 10:
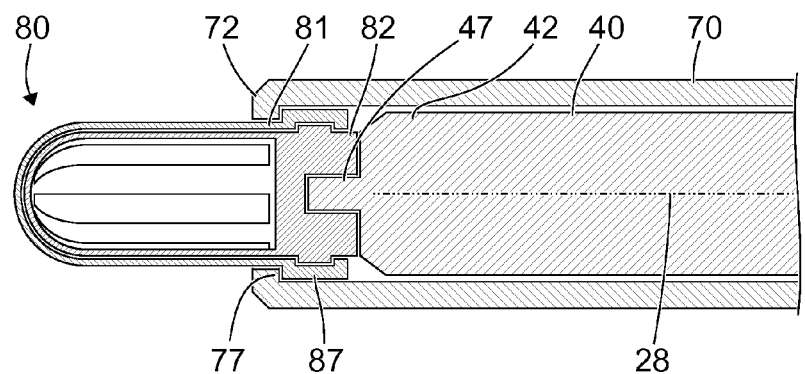
FIG. 10 shows a further schematic sectional representation of the tool from FIG. 9.

FIG. 10 shows a further schematic sectional representation of the tool 80, of the transferring rod 40 and of the outer shaft 70. The representation in FIG. 10 differs from the representation in FIG. 9 in particular in that the transferring rod 40 has been displaced in relation to the tool 80 in the first direction 91 indicated in FIG. 9 and the outer shaft 70 has been displaced in relation to the tool 80 in the second direction 92 indicated in FIG. 9.

By means of a movement of the transferring rod 40 in the first direction 93 in relation to the tool 80, the coupling 47 on the distal end 42 of the transferring rod 40 is inserted into the recess 84 on the second component part 82 of the tool 80. As already mentioned, the recess 84 on the second component part 82 of the tool 80 and the coupling 47 on the distal end 42 of the transferring rod 40 have corresponding cross sections which are not rotationally symmetrical with respect to the longitudinal axis 28. As a result, the transferring rod 40 and the second component part 82 of the tool 80 in the configuration shown in FIG. 10 are coupled with the effect that a rotation of the transferring rod 40 about the longitudinal axis 28 is combined with a corresponding rotation of the second component part 82 of the tool 80.

The outer shaft 70 is connected to the tool 80 by a movement in the second direction 94, which is opposite to the first direction 93, in relation to said tool. As already mentioned, the inwardly projecting collar 77 on the distal end 72 of the outer shaft 70 and the outwardly projecting collar 87 on the first component part 81 of the tool 80 are in each case not rotationally symmetrical with respect to the longitudinal axis 28. Consequently, the outer shaft 70 and the first component part 81 of the tool 80 are coupled together in the configuration shown in FIG. 10 with respect to a rotation about the longitudinal axis 28.

Figure 11:
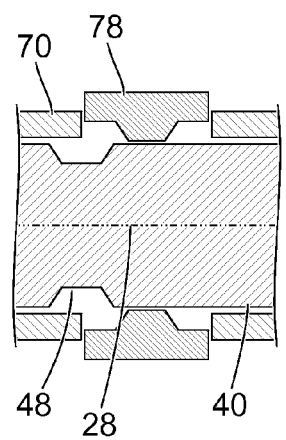
FIG. 11 shows a schematic sectional representation of an outer shaft and a transmitting device.

FIG. 11 shows a schematic sectional representation of the outer shaft 70 and of the transferring rod 40 from FIGS. 9 and 10 in the vicinity of their proximal ends. The sectional plane of FIG. 11 includes the longitudinal axis 28 and corresponds to the sectional planes of FIGS. 9 and 10. In each of two recesses located opposite one another, the outer shaft 70 includes a locking bar 78 which is movable in the radial direction. The transferring rod 40 has a ring-shaped circumferential groove 48. In the case of the configuration shown in FIG. 11, the locking bars 78 abut on the outside against the lateral surface of the transferring rod 40 outside the groove 48.

Figure 12:
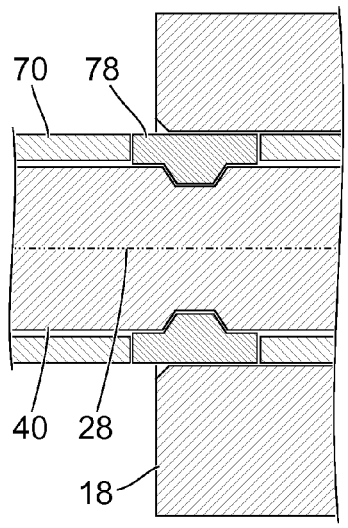
FIG. 12 shows a further schematic sectional representation of the outer shaft and the transmitting device from FIG. 11.

FIG. 12 shows a further schematic sectional representation of the outer shaft 70 and of the transferring rod 40. The representation in FIG. 12 corresponds to the representation in FIG. 11 with respect to the sectional plane shown and the detail selected. Compared to the representation in FIG. 11, however, the transferring rod 40 has been displaced in relation to the outer shaft 70 so far that the locking bars 78, displaced radially inward, engage in the groove 48 on the transferring rod 40. As a result, the locking bars 78 are closed off flush with the outside lateral surface of the outer shaft 70, and the entire arrangement of the outer shaft 70 and the transferring rod 40 can be inserted into a recess of corresponding cross section in a handling device 18.

In the case of the configuration shown in FIG. 12, radially outside surfaces of the locking bars 78 abut against the inside surface of the recesses in the handling device 18 and radially inside surfaces of the locking bars 78 abut against the transferring rod 40, in particular against its surface in the region of the groove 48. As a result, radial movements of the locking bars 78 and axial displacement of the transferring rod 40 in relation to the outer shaft 70 are excluded in a positive locking manner. The transferring rod 40 is, therefore, locked in relation to the outer shaft 70 with respect to axial displacement. Rotation of the transferring rod 40 in relation to the outer shaft 70, however, is just as possible as a common axial translation of the transferring rod 40 and the outer shaft 70 together.

Consequently, the locking bars 78 in the representation in FIG. 11 assume unlocking positions and in the representation in FIG. 12 they assume locking positions.

Figure 13:
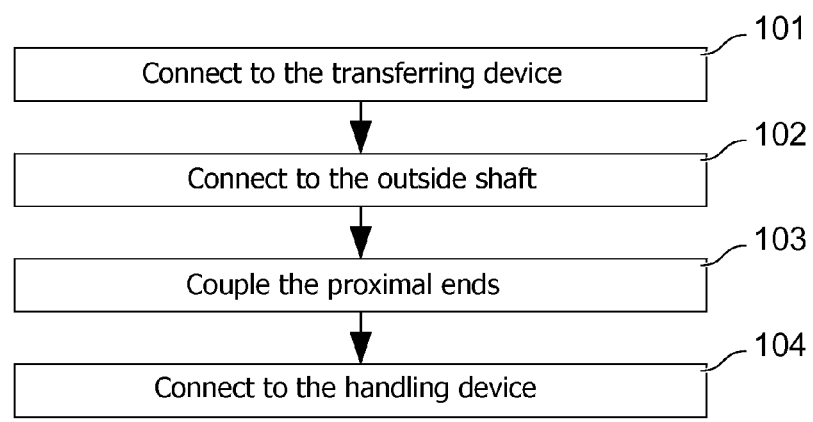
FIG. 13 shows a schematic flow diagram of a method for fitting together a medical instrument.

FIG. 13 shows a schematic flow diagram of a method for fitting together a tool, a transmitting device and an outer shaft to form a medical instrument. The method can also be carried out using tools, transmitting devices and outer shafts which differ from those shown above by way of FIGS. 1 to 12. Nevertheless, references from FIGS. 1 to 12 are used below as an example in order to facilitate comprehension.

In a first step 101, a tool 30, 50, 80 and a transmitting device 40, 60 are connected, the connecting process including a movement of the transmitting device 40, 60 in relation to the tool 30, 50, 80 in a first direction 91, 93. In a second step 102, the tool 30, 50, 80 and an outer shaft 70 are connected, the connecting process including a movement of the outer shaft 70 in relation to the tool 30, 50, 80 in a second direction 92, 94 which is opposite to the first direction 91, 93. In a third step 103, the proximal end of the outer shaft 70 and the proximal end 61 of the transmitting device 40, 60 are coupled in such a manner that the outer shaft 70 and the transmitting device 40, 60 are not movable in relation to one another in a parallel manner with respect to the first and to the second direction. The third step 103 includes, in particular, a movement of one or several locking bars 76, 78 in radial directions from unlocking positions into locking positions. In a fourth step 104, the proximal end of the outer shaft 70 is mechanically connected to a handling device 18. In this case, in particular, the locking bars 76, 78 are fixed in a positive locking manner in their locking positions.

REFERENCES

10 Medical instrument
11 Proximal end of the medical instrument 10
12 Distal end of the medical instrument 10
18 Handling device on the proximal end 11 of the medical instrument 10
19 Locking device on the handling device 18
20 Shaft of the medical instrument 10
21 Proximal end of the shaft 20
22 Distal end of the shaft 20
28 Longitudinal axis of the shaft 20
30 Gripping device on the distal end 12 of the medical instrument 10
31 Proximal end of the gripping device 30
32 Fixed mouth part of the gripping device 30
34 Pivotable mouth part of the gripping device 30
37 Carrier on the proximal end 31 of the gripping device 30
40 Transferring rod of the medical instrument 10
42 Distal end of the transferring rod 40
45 Groove in the transferring rod 40
46 Insulating covering on the transferring rod 40
47 Coupling on the distal end 42
48 Circumferential groove in the transferring rod 40
50 Cutting device on the distal end 12 of the medical instrument 10
51 Proximal end of the cutting device 50
52 Distal end of the cutting device 50
53 Cutting edge on the cutting device 50
56 Projection on the proximal end 51 of the cutting device 50
60 Inside shaft of the medical instrument 10
61 Proximal end of the inside shaft 60
62 Distal end of the inside shaft 60
63 Axial portion of an L-shaped slot on the distal end 62
64 Circumferential portion of an L-shaped slot on the distal end 62
65 Coupling component on the proximal end 61 of the inside shaft 60
66 Insulating component on the inside shaft 60
67 Metal component of the inside shaft 60
68 Flattening on the metal component 67 of the inside shaft 60
69 Insulating covering on the inside shaft 60
70 Outer shaft of the medical instrument 10
72 Distal end of the outer shaft 70
73 Axial portion of an L-shaped slot on the distal end 72
74 Circumferential portion of an L-shaped slot on the distal end 72
76 Locking bar in the outer shaft 70
77 Inwardly projecting collar on the distal end 72 of the outer shaft 70
78 Locking bar in the outer shaft 70
80 Tool
81 First component part of the tool 80
82 Second component part of the tool 80
84 Recess on the second component part of the tool 80
87 Outwardly projecting collar on the first component part 81 of the tool 80
91 First direction
92 Second direction 93 First direction
94 Second direction
101 First step (connecting the transmitting device)
102 Second step (connecting the outer shaft)
103 Third step (connecting the transmitting device)
104 Fourth step (coupling the proximal ends)

The invention claimed is:

1. A medical instrument, having:
an outer shaft, a distal end of the outer shaft having a tool coupling device;
a tool having an outer shaft coupling device and a transmitting coupling device;
a transmitting device configured to be disposed in the outer shaft for transmitting at least either a force or a torque to the tool, a distal end of the transmitting device having a tool attachment device;
the outer shaft coupling device is detachably mechanically connected to the tool coupling device via a movement of the outer shaft in relation to the tool in a first direction;
the transmitting coupling device is detachably mechanically connected to the tool attachment device via a movement of the transmitting device in relation to the tool in a second direction;
wherein the first direction is opposite to the second direction; and
wherein the movement of the outer shaft in relation to the tool in the first direction comprises a rotation of the outer shaft in relation to the tool in a first circumferential direction and wherein the movement of the transmitting device in relation to the tool in the second direction comprises a rotation of the transmitting device in relation to the tool in a second circumferential direction.

2. The medical instrument according to claim 1, where at least either the outer shaft coupling device and the tool coupling device or the transmitting coupling device and the tool attachment device include bayonet couplings.

3. The medical instrument according to claim 1, where the transmitting device includes an inside shaft.

4. The medical instrument according to claim 3, wherein the transmitting device comprises a transferring rod for transferring at least either the force or the torque, and wherein the transferring rod is configured for controlling a first function and the inside shaft is configured for controlling a second function.

5. The medical instrument according to claim 4, where
the transferring rod is coupled with a pivotable mouth part of the tool, and
the inside shaft is configured to detachably mechanically connect to a cutting device of the tool, the cutting device being disposed within and movable along a longitudinal groove of the transferring rod.

6. The medical instrument according to claim 5, where
a proximal end of the cutting device includes a projection which protrudes out of the longitudinal groove of the transferring rod and in a direction at right angles relative to a direction of movement of the cutting device within the longitudinal groove of the transferring rod,
the inside shaft of the transmitting device includes an L-shaped slot or an L-shaped groove for engaging the projection.

7. The medical instrument according to claim 5, where the tool has two mouth parts which are electrically insulated from one another,
a first of the two mouth parts is connected to the transferring rod so as to be electrically conductive,
a second of the of the two mouth parts is connected to the outer shaft so as to be electrically conductive.

8. The medical instrument according to claim 7, where the inside shaft has a distal portion and a proximal portion which is electrically insulated from the distal portion.

9. The medical instrument according to claim 3, further comprising:
a handling device that is detachably mechanically connected to a proximal end of the outer shaft and to a proximal end of the transmitting device,
wherein the handling device, the outer shaft and the transmitting device are configured such that the outer shaft and the transmitting device are immovable in relation to one another in a direction parallel to the first direction and to the second direction when they are mechanically connected to the handling device.

10. The medical instrument according to claim 9, where
the outer shaft includes a locking bar which is movable between an unlocking position and a locking position and is configured to engage in a corresponding recess on the transmitting device in the locking position,
the handling device is configured to hold the locking bar in the locking position when the outer shaft is mechanically connected to the handling device.

11. The medical instrument according to claim 9, where the outer shaft and the inside shaft are movable together in relation to the handling device in the direction parallel to the first direction and to the second direction when they are mechanically connected to the handling device.

12. The medical instrument according to claim 1, wherein the tool coupling device and the transmitting coupling device as well as the tool attachment device and the outer shaft coupling device are configured so that their respective detachable mechanical connections are formed asynchronously.

13. A method for fitting together a tool, a transmitting device and an outer shaft to form a medical instrument, the transmitting device configured for transferring at least either a force or a torque to the tool, said method comprising the following steps:
mechanically connecting the transmitting device to the tool, wherein the mechanically connecting includes moving the transmitting device in relation to the tool in a first direction;
mechanically connecting the outer shaft to the tool, wherein mechanically connecting includes moving the outer shaft in relation to the tool in a second direction; and
coupling a proximal end of the outer shaft and a proximal end of the transmitting device in such a manner that the outer shaft and the transmitting device, when coupled, are immovable in relation to one another in a direction which is parallel to the first direction and in a direction which is parallel to the second direction;
wherein the first direction is opposite to the second direction.

14. The method according to claim 13, said method additionally comprising the following step:
mechanically connecting the proximal end of the outer shaft to a handling device, wherein the step of coupling the proximal end of the outer shaft and the proximal end of the transmitting device is effected during the step of mechanically connecting the proximal end of the outer shaft to the handling device.

\* \* \* \* \*